United States Patent [19]
Hillen et al.

[11] Patent Number: 5,508,176
[45] Date of Patent: Apr. 16, 1996

[54] RECOMBINANT DNA, TRANSFORMED HOST MICROORGANISM AND METHOD FOR PRODUCING A POLYPEPTIDE HAVING MUTAROTASE ACTIVITY

[75] Inventors: Wolfgang Hillen; Robert Schmucker; Ulrike Guelland, all of Erlangen, Germany

[73] Assignee: Merck Patent Gesellshaft mit Beschrankter Haftung, Darmstadt, Germany

[21] Appl. No.: 243,541

[22] Filed: Sep. 12, 1988

[30] Foreign Application Priority Data

Sep. 12, 1987 [DE] Germany .................... 37 30 712.6

[51] Int. Cl.⁶ .................... C12P 21/06; C12N 15/00; C12N 1/20; C07H 21/04
[52] U.S. Cl. .................... 435/69.1; 435/71.2; 435/172.3; 435/233; 435/320.1; 435/252.33; 435/849; 536/23.1; 536/23.2; 930/240; 935/14; 935/19; 935/23; 935/28; 935/41; 935/59; 935/61; 935/73
[58] Field of Search .................... 435/69.1, 172.3, 435/233, 320.1, 252.33, 71.2, 849; 536/27.1, 23.1, 23.2; 930/240; 935/14, 19, 23, 28, 41, 59, 61, 73

[56] References Cited

U.S. PATENT DOCUMENTS 4,963,488 10/1990 Gatz et al. .................... 435/233

OTHER PUBLICATIONS

"Principles of Gene Manipulation", Old & Primrose; Blackwell Scientific Publications; 1985.
Bachmair, A. et al., "In Vivo Half–life of a Protein Is a Function of Its Amino Terminal Residue", *Science*, vol. 234, pp. 179–186, 1986.
Gatz, C. et al. "*Acinetobacter Calcoaceticus* encoded Mutarotase: Nucleotide Sequence Analysis of a Gene and Characterization of its Secretion in *E. coli,*" *Nucleic Acids Research* vol. 14, pp. 4309–4323 (1986).
Lambert, P. F. et al., "Use of Transcriptional Repressors to Stabilize Plasmid Copy Number of Transcriptional Fusion Vectors," *J. Bacteriology* vol. 162, 1, pp. 441–444 (1985).

*Primary Examiner*—David M. Naff
*Attorney, Agent, or Firm*—Millen, White, Zelano, & Branigan

[57] ABSTRACT

A polypeptide having mutarotase activity is obtained from a host microorganism that has been transformed with a molecule having a recombinant DNA sequence. The molecule having a recombinant DNA sequence is prepared by removing the first 60 nucleotides of a DNA sequence originating from the genome of *Acinetobacter calcoaceticus* that codes for the polypeptide, modifying the following 21 nucleotides and fusing of the resultant structural gene with the start of the tetracycline-repressor gene and with an effective promotor sequence. The tetracycline-regressor gene and the promotor sequence preferably originate from the same microorganism such as *E. coli* in which expression of the polypeptide is carried out, and result in increased yield of the expressed polypeptide having mutarotase activity.

11 Claims, 4 Drawing Sheets

```
                    (A)                           (B)
                     ↓                             ↓
a:      ATG-ATG-TCT-AGA-TTG-AAT-GTA-AAA-CCA-TAT-GGT-
        ACG-ACT-CAA-AAT-GGC-CAA-AAA-GTT-GAT-CTA-
        TAC-ACC-ATG-AGT-AAT-AAC-AAT-GGA-GTC-TCG-
        GTA-TCT-TTT-ATT-AGT-TTT-GGT-GGT-GTA-ATT-
        ACA-CAA-ATC-TTG-ACT-CCC-GAT-GCC-CAA-GGC-
        AAA-CAA-AAT-AAT-ATC-GTT-TTG-GGC-TTT-GAT-
        GAC-TTA-AAA-GGC-TAT-GAA-GTC-ACT-GAT-ACC-
        AAG-GAA-GGT-ATT-CAT-TTT-GGC-GGA-TTA-ATT-
        GGT-CGT-TAT-GCG-AAC-CGG-ATT-GGC-AAT-GCT-
        AAA-TTT-AGC-TTA-GAT-GGA-AAA-ACG-TAT-AAC-
        CTC-GAA-AAA-AAT-AAT-GGT-CCG-AAC-TCA-TTA-
        CAT-AGC-GGC-AAT-CCT-GGT-TTT-GAT-AAA-CGT-
        GTT-TGG-CAA-GTT-AAG-CCC-CTC-GTT-TCT-AAA-
        GGT-GAA-ACC-GTT-AAA-GCT-TCT-CTT-AAG-TTA-
        ACC-AGC-CCA-AAT-GGA-GAT-CAA-GGT-TTT-CCC-
        GGA-AAA-TTA-GAT-GTA-GAA-GTG-ATC-TAC-AGT-
        CTT-TCA-GAT-CAA-AAT-GAA-TTC-AAG-ATT-GAA-
        TAT-AAA-GCC-AAA-ACT-GAT-CAG-CCT-ACA-GTC-
        GTC-AAC-CTT-ACC-AAC-CAC-AGT-TAT-TTC-AAC-
        TTA-TCA-GGT-GCT-GGG-AAC-AAT-CCT-TAT-GGC-
        GTG-CTA-GAT-CAT-GTG-GTA-CAA-CTC-AAT-GCA-
        GGC-CGT-ATT-CTG-GTA-ACC-GAT-CAA-AAC-TCT-
        TTA-CCA-ACA-GGT-GAA-ATT-GCT-TCA-GTT-GCA-
        GGT-ACG-CCT-TTT-GAT-TTT-CGG-ATG-CCT-AAA-
        GCA-ATC-GTA-AAA-GAT-ATT-CGA-GCA-AAT-AAT-
        CAG-CAA-TTG-GCC-TAT-GGA-TAT-GGC-TAT-GAC-
        CAA-ACT-TGG-GTA-ATT-AAT-CAA-AAG-TCT-CAA-
        GGA-AAA-CTC-AAT-CTT-GCA-GCT-ATT-GTG-GTT-
        GAT-CCA-AAA-TCT-AAA-CGG-ACC-ATG-CAA-GTC-
        TTA-ACC-ACT-GAA-CCA-AGC-GTC-CAA-ATG-TAT-
        ACA-GCC-GAT-CAT-TTA-TTA-GGA-AAT-ATT-GTT-
        GGC-GCA-AAT-GGC-GTA-CTC-TAT-CGA-CAA-GCA-
        GAC-GCA-CTA-GCA-TTA-GAA-ACA-CAG-CAT-TTT-
        CCA-GAC-AGC-CCG-AAT-CAA-CCA-ACT-TTC-CCG-
        TCT-ACA-CGT-TTA-AAC-CCA-AAT-CAA-ACT-TAT-
        AAC-AGT-GTT-ACC-GTA-TTT-AAG-TTT-GGT-GTT-
        CAA-AAA b:      -GCA-ACG-TTG-AAT-GTA-AAA-CCA-
```

```
                        (A)                              (B)
                         ↓                                ↓
a:    SER-ARG-LEU-ASN-VAL-LYS-PRO-TYR-GLY-THR-THR-GLN-
      ASN-GLY-GLN-LYS-VAL-ASP-LEU-TYR-THR-MET-SER-ASN-
      ASN-ASN-GLY-VAL-SER-VAL-SER-PHE-ILE-SER-PHE-GLY-
      GLY-VAL-ILE-THR-GLN-ILE-LEU-THR-PRO-ASP-ALA-GLN-
      GLY-LYS-GLN-ASN-ASN-ILE-VAL-LEU-GLY-PHE-ASP-ASP-
      LEU-LYS-GLY-TYR-GLU-VAL-THR-ASP-THR-LYS-GLU-GLY-
      ILE-HIS-PHE-GLY-GLY-LEU-ILE-GLY-ARG-TYR-ALA-ASN-
      ARG-ILE-GLY-ASN-ALA-LYS-PHE-SER-LEU-ASP-GLY-LYS-
      THR-TYR-ASN-LEU-GLU-LYS-ASN-ASN-GLY-PRO-ASN-SER-
      LEU-HIS-SER-GLY-ASN-PRO-GLY-PHE-ASP-LYS-ARG-VAL-
      TRP-GLN-VAL-LYS-PRO-LEU-VAL-SER-LYS-GLY-GLU-THR-
      VAL-LYS-ALA-SER-LEU-LYS-LEU-THR-SER-PRO-ASN-GLY-
      ASP-GLN-GLY-PHE-PRO-GLY-LYS-LEU-ASP-VAL-GLU-VAL-
      ILE-TYR-SER-LEU-SER-ASP-GLN-ASN-GLU-PHE-LYS-ILE-
      GLU-TYR-LYS-ALA-LYS-THR-ASP-GLN-PRO-THR-VAL-VAL-
      ASN-LEU-THR-ASN-HIS-SER-TYR-PHE-ASN-LEU-SER-GLY-
      ALA-GLY-ASN-ASN-PRO-TYR-GLY-VAL-LEU-ASP-HIS-VAL-
      VAL-GLN-LEU-ASN-ALA-GLY-ARG-ILE-LEU-VAL-THR-ASP-
      GLN-ASN-SER-LEU-PRO-THR-GLY-GLU-ILE-ALA-SER-VAL-
      ALA-GLY-THR-PRO-PHE-ASP-PHE-ARG-MET-PRO-LYS-ALA-
      ILE-VAL-LYS-ASP-ILE-ARG-ALA-ASN-ASN-GLN-GLN-LEU-
      ALA-TYR-GLY-TYR-GLY-TYR-ASP-GLN-THR-TRP-VAL-ILE-
      ASN-GLN-LYS-SER-GLN-GLY-LYS-LEU-ASN-LEU-ALA-ALA-
      ILE-VAL-VAL-ASP-PRO-LYS-SER-LYS-ARG-THR-MET-GLN-
      VAL-LEU-THR-THR-GLU-PRO-SER-VAL-GLN-MET-TYR-THR-
      ALA-ASP-HIS-LEU-LEU-GLY-ASN-ILE-VAL-GLY-ALA-ASN-
      GLY-VAL-LEU-TYR-ARG-GLN-ALA-ASP-ALA-LEU-ALA-LEU-
      GLU-THR-GLN-HIS-PHE-PRO-ASP-SER-PRO-ASN-GLN-PRO-
      THR-PHE-PRO-SER-THR-ARG-LEU-ASN-PRO-ASN-GLN-THR-
      TYR-ASN-SER-VAL-THR-VAL-PHE-LYS-PHE-GLY-VAL-GLN-
      LYS b:      -ALA-THR-LEU-ASN-VAL-LYS-PRO-
``` pWH 1256

```
            XbaI                           NdeI
             ↓                              ↓
5' ----TTAATGATG|TCTAGA|TTGAATGTAAAAC|CATATG|GTACG----
3' ----AATTACTAC|AGATCT|AACTTACATTTTG|GTATAC|CATGC----
         |Met|Ser|Arg|Leu|Asn|Val|Lys|Pro|Tyr|Gly|Thr
```

Ala Thr

RECOMBINANT DNA, TRANSFORMED HOST MICROORGANISM AND METHOD FOR PRODUCING A POLYPEPTIDE HAVING MUTAROTASE ACTIVITY

Background of the Invention

The invention relates to the provision of recombinant DNA sequences and transformed host organisms which code for a polypeptide having the biological activity of mutarotase.

The invention additionally relates to cloning and expression vectors for use for the preparation of a polypeptide having the biological activity of mutarotase, as well as to host organisms transformed with such vectors, for example bacteria, yeasts, other fungi, animal or human cells.

Finally, the invention relates to the use of the said polypeptide having the biological activity of the enzyme mutarotase to increase the rate of enzymatic detection reactions or reactions of aldoses.

Mutarotase (aldose-1-epimerase, EC 5.1.3.3) is known to increase the rate of attainment of equilibrium between the α- and β-anomers of aldohexoses, for example between α- and β-glucose or α- and β-galactose. The main use of the enzyme is in analytical biochemistry to increase the rate of enzymatic detection reactions for aldoses with the aid of the enzymes specific for the α- or β-form, in which the attainment of equilibrium between the two anomers is the rate-determining step, for example in determination methods using glucose dehydrogenase, glucose oxidase or galaclose dehydrogenase.

Mutarotase activity is determined in a manner known per se by measurement of the increase in the reaction rate for glucose conversion with, for example, glucose dehydrogenase. This method is among the standard methods, for example in clinical chemistry. It entails mutarotase, glucose dehydrogenase and NAD being reacted with a freshly prepared solution of α-glucose, and the $NADH_2$ which is formed being determined by measurement of the extinction at 366 nm. Measurement of the increase in the rate of $NADH_2$ formation by mutarotase compared with a comparison figure allows the mutarotase activity in the solution used to be calculated.

Mutarotase is widespread in nature; it occurs in various microorganisms (bacteria, yeasts and filamentous fungi), in plants and in animal tissues.

Reasonable enzyme contents allowing isolation of mutarorase on the industrial scale have hitherto been found only in the kidneys of mammals (cattle, pigs); all the known commercial products are prepared from kidneys. The working-up processes for this are as a rule very elaborate, and large amounts of starting material are required. The first description of a process for the microbiological preparation of mutarotase from strains of Aspergillus niger is given in Blochim. Biophys. Acta 662, 285 (1981). According to this, a mutarotase activity of 4.4 U/L of culture broth was obtained from the best strain.

However, the yield of mutarotase is relatively low by this process. In addition, the properties of the enzyme from Aspergillus niger, especially when used for enzymatic determinations, are unfavorable. German Offenlegungsschrift 3,531,360 discloses that mutarotase activities of 50–100 U/L of culture broth can be obtained by classicial microbial processes in optimized strains of Acinetobacter calcoaceticus. Compared with this, the same Offenlegungsschrift describes a genetic engineering process in which a polypeptide which has the biological activity of mutarotase and which is encoded by a DNA which preferably originates from the genome of Acinetobacter calcoaceticus is expressed in a transformed E. coli host. In this, mutarotase activities averaging about 5000 U/L of culture broth are obtained. However, even these activities and yields of mutarotase which are themselves a great improvement over classical processes still appear insufficient.

SUMMARY OF THE INVENTION

This invention provides DNA sequences and polypeptide which allow the preparation of mutarotase in a genetic engineering process in distinctly higher yields than hitherto and with good enzyme properties.

It has been found, surprisingly, that deletion of the first 60 nucleotides of the DNA sequence which is indicated in German Offenlegungsschrift 3,531,360 and codes for a polypeptide having the biological activity of mutarotase, slight modifications, which are further specified hereinafter, within the following 21 nucleotides of the structural gene, and fusion of this new structural gene with the start of the tetracycline-repressor gene and with an effective promoter sequence, both of which preferably originate from the same microorganism in which the expression of the enzyme is carried out, result in a new recombinant DNA molecule which brings about in the transformed host organism the expression of stable mutarotase, with the enzyme activities which can be obtained being a factor of 10 to 50 higher than in the obtaining of mutarotase by the genetic engineering process of German Offenlegungsschrift 3,531,360. So the presence of parts of the tetracycline repressor gene in combination with the described promoter region has, surprisingly, a significant impact in increasing the yield of expressed mutarotase. The properties of the mutarorase prepared by the process according to the invention equal the advantageous properties of the enzyme obtained in German Offenlegungsschrift 3,531,360, which is equivalent to U.S. Ser. No. 903,319, filed Sep. 3, 1986, now U.S. Pat. No. 9,963,488, both of which are incorporated by reference herein. Hence the invention relates to a recombinant DNA sequence coding for a polypeptide having the biological activity of mutarotase, characterized in that it contains the structural gene from the genome of a mutarotase-producing microorganism, the start of the tetracycline-repressor gene and a promoter sequence, with the tetracycline-repressor sequence region and the promoter sequence originating from the microorganism in which the expression of the structural gene is carried out.

The invention particularly relates to a DNA sequence which codes for a polypeptide having the biological activity of mutarotase and which corresponds to the structural gene, characterized in that it has the nucleotide sequence indicated in FIG. 1 (a, b).

The invention further relates to a polypeptide having the biological activity of mutarotase, characterized in that it has the amino acid sequence indicated in FIG. 1 (a, b).

The invention also particularly relates to the expression plasmid which is called pWH 1256 and has the deposit number DSM 4228 P, and to its mutants and variants.

The invention furthermore relates to a host organism containing the recombinant DNA according to the invention, especially E. coli WH 1256 with the deposit number DSM 4227, and to its mutants and variants.

Furthermore, the invention relates to a process for the preparation of a polypeptide having a biological activity of mutarotase by cultivation of a microorganism in a nutrient medium and isolation of the polypeptide formed by expression, characterized in that the microorganism used is a host organism transformed with at least one recombinant DNA molecule according to the invention.

In addition, the invention relates to the use of a polypeptide having the biological activity of mutarotase and the amino acid sequences indicated in FIG. 2 (a, b) for increasing the rate of enzymatic reactions of aldoses.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

FIG. 1: DNA sequence of the structural gene region coding for a polypeptide having the biological activity of mutarotase a: DNA sequence present in the plasmid pWH 1256 b: alternative sequence between positions (A) and (B)

Figure 3:
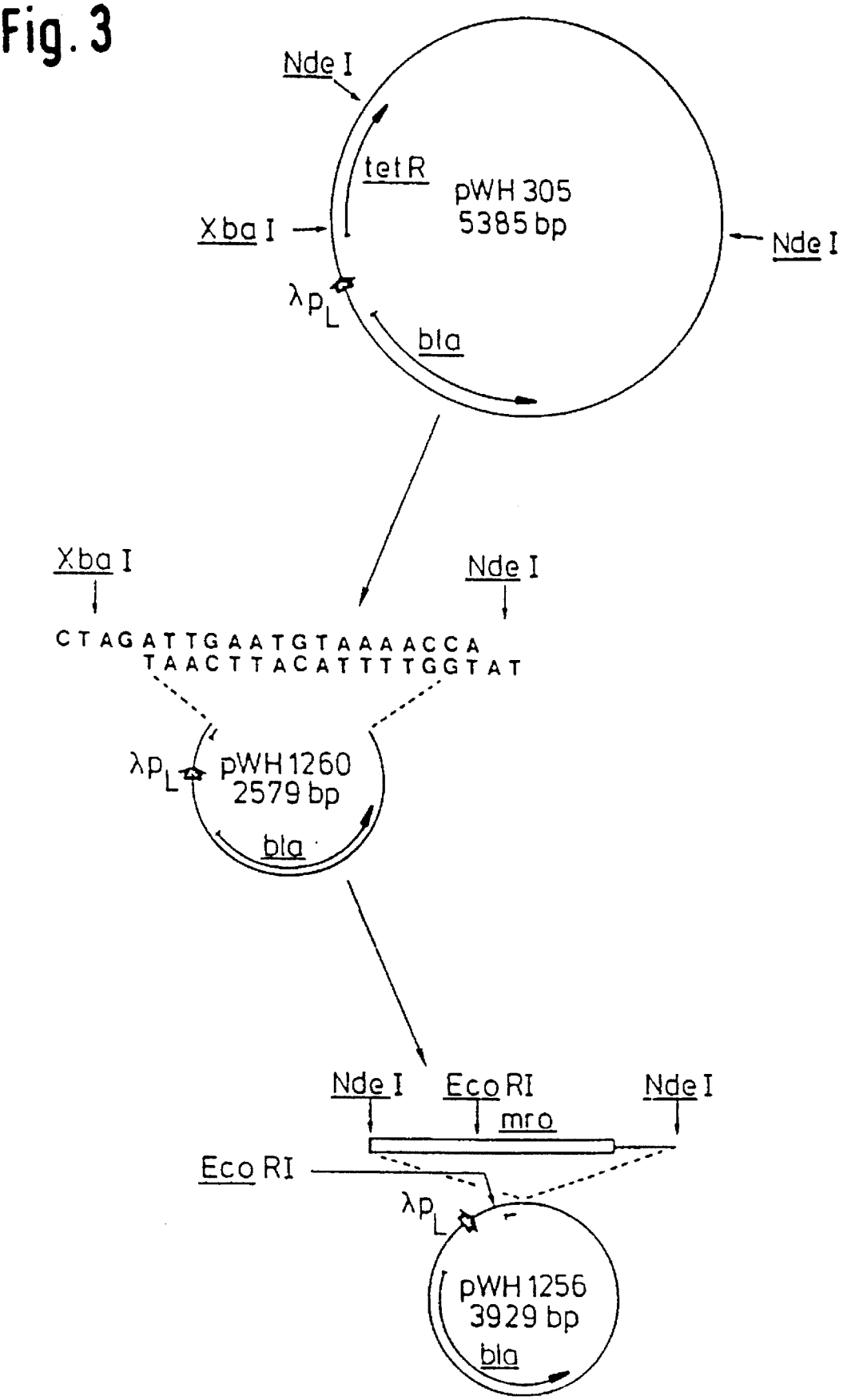

FIG. 2:

a: amino acid sequence of the expression product of pWH 1256 b: alternative sequence between positions (A) and (B)

FIG. 3: Construction of the expression plasmid pWH 1256 from the plasmids pWH 305 and pWH 1372. pWH 305 contains the tetR region and the λPL promoter from *E. coli*. pWH 1372 contains a mutarotase-coding gene region from *Acinetobacter calcoaceticus*.

FIG. 4: Nucleotide sequence from pWH 1256 in the region of the start of the mutarotase gene. The cuts made by the restriction enzymes XbaI and NdeI, which are preferably used, as well as the amino acids assigned thereto, are shown in the drawing.

DETAILED DESCRIPTION

The term "polypeptide having the biological activity of the enzyme mutarotase" designates a polypeptide or protein whose amino acid sequence corresponds to the natural mutarotase from *Acinetobacter calcoaceticus*, is similar to this amino acid sequence or embraces only a section thereof. Corresponding fusion proteins are also designated according to the invention as "polypeptides having the biological activity of the enzyme mutarotase."

The DNA molecules, polypeptides, expression plasmids and host organisms as described above and below embrace as well all kinds of routants or variants thereof caused e.g., by radiation, temperature effects, chemical or biological influences, whenever they exhibit the biological activity of mutarotase.

Suitable host organisms into which the mutarotase-coding DNA can be inserted are primarily microorganisms, but also plant, animal or human cells. Microorganisms are preferred, such as bacteria, yeasts and filamentous fungi. *E. coli* bacteria are particularly preferably used.

Tetracycline-resistance genes, including the tetracycline repressor, are likewise known (for example E. Winnacker, in: Gene und Klone (Genes and Clones), VCH (1985)). The tetracycline-repressor genes used according to the invention originate from the host organism, and therefore have the same origin as the promoter region which controls the complete coding region of the mutarotase gene.

The term "a sequence originating from the beginning of a tetracycline repressor gene" designates a DNA sequence comprising the start codon (ATG) and the Shine Dalgarno Sequence of the tetracycline repressor gene.

Thus, the promoter and tetracycline-repressor genes from *E. coli* are preferably used.

In principle, all promoters which bring about effective expression of mutarotase are suitable according to the invention as expression control sequences. Preferably used are *E. coli* promoter systems such as, for example, the *E. coli* λP$_L$ promoter system, the *E. coli* lac system, the *E. coli* β-lactamase system, the *E. coli* trp system or the *E. coli* lipoprotein promoter system. Particularly suitable is the λP$_L$ promoter, which is disclosed in European Published Specification 0,041,767, for example.

The following steps are preferably carried out to provide the genetic engineering process according to the invention for the preparation of a polypeptide having the biological activity of mutarotase:

The starting vectors are the plasmids pWH 305 and pWH 1372. The plasmid pWH 305 and its construction are adequately described by Oehmichen et al., (1984) EMBO J. 3, 539–543. pWH 305 contains the gene for the tetracycline repressor (tetR) and the λP$_L$ promoter from *E. coli*. pWH 1372 and its construction are disclosed in German Offenlegungsschrift 3,531,360 pWH 1372 contains a DNA sequence coding for a polypeptide having a biological activity of mutarotase. This DNA sequence originates from the genome of *Acinetobacter calcoaceticus*. The nucleotide sequence of the DNA, and the amino acid sequence of the polypeptide are depicted in German Offenlegungsschrift 3,531,360.

Firstly, pWH 305 is cut at the start of the tetR gene region (FIG. 3) and at approximately the opposite side by standard methods using known restriction enzymes. Suitable and preferred for the cut at the start of the tetR gene is the known restriction enzyme XboI. The restriction endonuclease NdeI is preferably used for the cut on the distal end of the gene. The cuts produce, inter alia, a vector fragment which contains the λP$_L$ promoter and the ampicillin-resistance gene. This vector fragment is then ligated with a double-stranded oligonucleotide of sequence I

in a manner known per se (Example 1). The oligonucleotides are synthesized by standard methods in a manner known per se and as described in detail in German Offenlegungsschrift 3,531,360. The product from this is the new plasmid pWH 1260. This plasmid is then cut open or linearized with a restriction endonuclease, preferably NdeI. The restriction of pWH 1372 with NdeI preferably takes place approximately at the start and a few nucleotides from the end of the mutarotase structural gene. The two vector fragments are ligated in a manner known per se. This results in the new expression plasmid pWH 1256 according to the invention (FIG. 3). After the expression vector pWH 1256 has been constructed it is inserted in a customary manner into a transformable host organism, preferably *E. coli*. A particularly suitable example is the known and readily obtainable *E. coli* strain No. 69 (*E. coli* K12ΔH1Δtrp) which contains on its chromosome a locus which codes for the thermolabile repressor cI 857. Hence in this strain the transcription controlled by the λ-P$_L$ promoter is completely inhibited at 3° C. but is not inhibited at 40° C., because at this temperature the thermolabile repressor cI 857 is in its inactive form.

Subsequently, the transformed host organism according to the invention is cultivated in a suitable nutrient medium in a manner known per se, and the polypspride which has the biological activity of mutarotase and is produced during expression is obtained therefrom by standard methods.

It is possible, according to the invention, to construct an alternative expression plasmid which is related to the vector pWH 1256 according to the invention, by ligating the vector fragment from pWH 305 in a manner analogous to that described above, with a synthetic double-stranded oligonucleotide of sequence II

which (including the nucleotide G at the 5' end of the top strand which was inserted as a substitute for the nucleotide T by site specific mutagenesis in a manner known per se) codes for the portion of the amino acid sequence indicated in FIG. 2b. The expression of mutarotale in E. coli host cells which have been transformed appropriately with the gene of FIG. 1b results in enzyme activities, yields and properties which are comparable with the figures stated hereinafter and in Example 2 for the polypeptide shown in FIG. 2a.

All the methods forming the basis for the process according to the invention, which is described above, such as, for example, DNA restriction, ligation, synthesis of oligonucleotides, DNA and amino acid sequence analyses, cloning and transformation, isolation and purification of the expression product are thoroughly well described in the literature and explained in detailed form in German Offenlegungsschrift 3,531,360.

The nucleotide sequence of the mutarotase structural gene according to the invention, which has high-level expression and is shown in FIG. 1a (starting from the synthesized oligonucleotide sequence I), corresponds to the sequence depicted in German Offenlegungsschrift 3,531,360 from nucleotide 80 (position 26 in FIG. 1a). Compared with the latter sequence, the sequence in FIG. 1a according to the invention contains at position 25 (position 79 in German Offenlegungsschrift 3,531,360) cytosine (C) in place of thymine (T). The sequence between nucleotide positions 60 and 70 (German Offenlegungsschrift 3,531,360) or 6 and 16 (FIG. 1a) has been changed from -GCA-ACG-TTA- to -TCT-AGA-TTG-. The first 60 nucleotides (German Offenlegungsschrift 3,531,360) have been replaced by the nucleotide sequence -ATGATG- in the sequence in FIG. 1a according to the invention.

Accordingly, the amino acid sequence starting from nucleotide position 7 emerges as -Ser-Arg-Leu-Asn-Val-Lys-Pro (FIG. 2a) in place of -Ala-Thr-Leu-Asn-Val-Lys-Ser (starting from nucleotide position 61 in German Offenlegungsschrift 3,531,360).

The DNA sequence in FIG. 1b, likewise according to the invention, (starting from the synthesized oligonucleotide sequence II) differs from the DNA sequence according to the invention as shown in FIG. 1a only between positions 6 and 13 by the sequence -GCA-ACG- in place of -TCT-AGA-. The amino acid sequence is correspondingly changed from -Ser-Arg- to -Ala-Thr- (FIG. 2b). Some of the changes are also illustrated in FIG. 4.

The alterations which have been described result in the process according to the invention providing a polypeptide having the biological activity of mutarotase in surprisingly high yields. Thus, for example, mutarotase activities of from 40,000 to 200,000, preferably from 100,000 to 150,000, units/L of culture broth can be obtained in a correspondingly transformed E. coli host. This is an increase in enzyme activity of about 30-fold compared with the process described in German Offenlegungsschrift 3,531,360. Comparison with mutarotase activities in optimized strains of Aspergillus niger and Acinetobacter calcoaceticus, some of which are still in use, obtainable by classical microbial processes in fact reveals an increase by a factor of about 30,000 and 3,000 respectively. The amounts yielded by the processes according to the invention vary between 200 and 800, preferably between 500 and 650, mg of mutarotase/L of culture medium.

The mutarotase expressed in E. coli by the process according to the invention can be isolated and purified in a manner which is just as straightforward and effective as that described in German Offenlegungsschrift 3,531,360. Moreover, it has the almost identical advantageous properties.

The mutarotase prepared by the process according to the invention is, by reason of these good properties and its very high activity, outstandingly suitable for increasing the rate of enzymatic reactions of aldoses.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding German application P 37 30 712 (the priority document), are hereby incorporated by reference.

EXAMPLES

Example 1

Construction of the expression plasmid pWH 1256 and transformation of E. coli 19 ug of pWH 305 (oehmichen et al., loc. cit.) are restricted with the restriction endonucleases XbaI and NdeI, and the vector fragment is eluted from an agarose gel after electrophoresis. The vector fragment contains the Ducleotide sequence "ATGATGI".

A double stranded oligonucleotide with the sequence

is synthesized as described in German Offenlegungsschrift 3,531,360 and is ligated in a 100-fold molar excess with the vector fragment. The reaction product is transferred to E. coli W6 in a manner known per se. E. coli W6 is disclosed in European Published Specification 0,041,767. The plasmid DNA is prepared from 50 ampicillin-resistant candidates by rapid digestion and is examined by restriction with XbaI and NdeI. A colony whose plasmid is linearized by both restriction endonucleases is characterized by double-strand dideoxy sequencing (Chen and Seeburg (1985), DNA 4; 165–170). This confirms the above sequence of the oligonucleotide as well as the sequences of the flanking vector regions (Postle et al. (1984), Nucleic Acids Res. 12, 4849–4863; Sutcliffe (1979). Cold Spring Harbor Symp Quant. Biol. 43, 77–90). The resulting plasmid is designated pWH 1260 and is prepared from 1 L of culture. 5 µg of pWH 1260 are linearized with the restriction endonuclease NdeI.

10 μg of pWH 1372 (German Offenlegungsschrift 3,531, 360) are digested with the restriction endonuclease NdeI, and the fragment which is 1350 bp in length is eluted from a 1% agarose gel in a customary manner. Equimolar amounts of linearized pWH 1260 DNA and the 1350 bp fragment from pWH 1372 are ligated and used to transform *E. coli* W6. Plasmid DNA from fifty ampicillin-resistant candidates is prepared by rapid digestion and electrophoresed on 1% agarose to check that insertion has taken place. The direction of insertion in recombinant colonies is checked by restriction with EcoRI. The plasmid with the tetR (pWH 305) mro (pWH 1372) fusion is called pWH 1256 and is prepared from 1 L of culture. For the expression of the fusion protein, the plasmid is transformed into *E. coli* K12ΔH1Δtrp (German Offenlegungsschrift 3,531,360) at 30° C. The resulting strain is designated *E. coli* WH 1256. The construction of pWH 1256 is depicted diagrammatically in FIG. 3.

Example 2

Expression of mutarotase with the expression plasmid pWH 1256 in *E. coli* 69

The *E. coli* strain NO. 69 (*E. coli* K12ΔH1Δtrp) is transformed with the recombinant expression plasmid pWH 1256 by standard methods. This host bacterial strain contains on its chromosome a locus which codes for the thermolabile repressor cI 857. Hence in this strain the transcription controlled by the $\lambda P_L$ promoter is completely inhibited at 32° C. but is not inhibited at 40° C., because at this temperature the thermotabile repressor cI 857 is in its active form.

In a typical expression procedure, 4 L of LB medium (10 g/L tryprone, 8 g/L NaCl, 5 g/L yeast extract, pH 7.8, 0.1 g/L ampicillin) in a fermenter are inoculated with 200 ml of an overnight culture of *E. coli* 69/pWH 1256, and cultivation is carried out at 28° C. until the cell density is 5 OD (650 nm). The culture is then heated to 42° C. and aerated further. The mutarotase activity is detected after the subsequent cell disruption.

1 ml of cell culture is removed, adjusted to 50 mM EDTA and incubated on ice for 10 min, 100 μl of lysozyme (10 mg/ml) are added, and incubation on ice is continued for 10 min. The cells are then lysed while cooling in ice. The cell detritus is then removed by centrifugation, and the supernatant is examined for mutarotase activity as indicated above. The measured figures for expression, of 150,000 U/L of culture medium, correspond to about 650 mg of mutarotase/L of culture medium.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A recombinant DNA molecule coding for a polypeptide having the biological activity of mutarotase and capable of being expressed in a host microorganism when combined with a vector, comprising, in a 5' to 3' direction:

a promoter sequence, operably linked to a Shine-Dalgarno sequence derived from the beginning of a tetracycline-repressor gene, operably linked to a first ATG starting codon, fused in frame with a recombinant structural gene coding for mutarotase derived from the genome of a mutarotase-producing microorganism of the genus Acinetobacter, wherein the genomic sequence of the Acinetobacter mutarotase gene from which the recombinant structural gene is derived comprises a second ATG starting codon, a leader sequence and a coding sequence, and the recombinant structural gene comprises a modified genomic Acinetobacter mutarotase sequence wherein the leader sequence has been removed, and the coding sequence directly fused in frame 3' to the second ATG starting codon has been modified to the nucleotide sequence

X TTG AAT GTA AAA CCA, wherein X is TCT AGA or CGA ACG;

wherein the Shine-Dalgarno sequence and the promoter sequence are derived from the host microorganism in which the mutarotase is capable of being expressed.

2. A DNA molecule according to claim 1, wherein the promoter sequence is derived from *Escherichia coli*.

3. An isolated second DNA molecule capable of hybridizing to a first DNA molecule according to claim 1, where the DNA sequence of said second DNA molecule is related to the DNA sequence of said first DNA molecule by specific and/or non-specific modifications, and said second DNA molecule codes for a polypeptide having the biological activity of mutarotase.

4. A host microorganism transformed with at least one recombinant DNA-molecule, according to claim 1.

5. A host mircoorganism according to claim 4, wherein the host microorganism is *Escherichia coli*.

6. A method for preparing a polypeptide having the biological activity of mutarotase comprising cultivating a host microorganism transformed with at least one recombinant DNA molecule according to claim 1 in a nutrient medium and isolating the polypeptide formed by expression of said structural gene.

7. A method for preparing a polypeptide having the biological activity of mutarotase comprising cultivating a host microorganism transformed with at least one isolated second recombinant DNA molecule according to claim 3 in a nutrient medium and isolating the polypeptide formed by expression of said structural gene.

8. An expression plasmid with the designation pWH 1256 and the deposit number DSM 4228 P, and its mutants and variants coding for a polypeptide having the biological activity of mutarotase.

9. A method for preparing a polypeptide having the biological activity of mutarotase comprising cultivating a host microorganism transformed with at least one expression plasmid according to claim 8 in a nutrient medium and isolating the polypeptide formed by expression of said plasmid.

10. A host micoorganism according to claim 5 with the designation *Escherichia coli* WH 1256 and the deposit number DSM 4227, and its mutants and variants which are capable of expressing the recombinant DNA molecule coding for a polypeptide having the biological activity of mutarotase.

11. A method for preparing a DNA molecule coding for a polypeptide having the biological activity of mutarotase, comprising digesting a pWH305 plasmid with the restriction endonucleases XbaI and NdeI, producing an intermediate plasmid by inserting between the thus produced restriction sites a synthetic double stranded oligonucleotide of the sequence

5' CTAGATTGAATGTAAAACCA 3'
    3'       TAACTTACATTTTGGTAT 5',

5' CTAGATTGAATGTAAAACCA 3'
3' TAACTTACATTTTGGTAT 5' digesting the intermediate plasmid with NdeI, and inserting into the thus produced NdeI restriction site the mutarotase gene-containing fragment of a NdeI-digested pWH1372 plasmid.

* * * * *